(12) United States Patent
Stein et al.

(10) Patent No.: US 6,288,286 B1
(45) Date of Patent: Sep. 11, 2001

(54) METHOD FOR PRODUCING HEXANEDIOL-1,6

(75) Inventors: Frank Stein, Bad Dürkheim; Thomas Krug, Worms; Martin Gall, Mutterstadt; Gabriele Iffland, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/700,366
(22) PCT Filed: May 10, 1999
(86) PCT No.: PCT/EP99/03193
§ 371 Date: Nov. 15, 2000
§ 102(e) Date: Nov. 15, 2000
(87) PCT Pub. No.: WO99/62852
PCT Pub. Date: Dec. 9, 1999

(30) Foreign Application Priority Data

May 29, 1998 (DE) .............................. 198 26 614

(51) Int. Cl.$^7$ .................................................. C07C 27/00
(52) U.S. Cl. ......................... 568/864; 568/852; 568/853; 568/854
(58) Field of Search ................... 568/864, 853, 568/852, 854

(56) References Cited

U.S. PATENT DOCUMENTS

| 3,551,300 | 12/1970 | Longley . |
| 4,482,764 | 11/1984 | Herrmann . |

FOREIGN PATENT DOCUMENTS

| 28 19 593 | 11/1979 | (DE) . |
| 195 14930 | 10/1996 | (DE) . |
| 97/31182 | 9/1997 | (WO) . |
| 97/31883 | 9/1997 | (WO) . |
| WO97/31882 | * 9/1997 | (WO) . |

OTHER PUBLICATIONS

Houben–Weyl, Methoden der Organischen Chem. vol. IV/1c 1980, pp. 16–26 and 45–67.*
Houben–Weyl, Methoden der Organischen Chem. vol. IV/1c Georg Thieme Verlag 1980, p. 45–67 & 16–26.

* cited by examiner

Primary Examiner—Samuel Barts
Assistant Examiner—Elvis O. Price
(74) Attorney, Agent, or Firm—Keil & Weinkauf

(57) ABSTRACT

A process for preparing 1,6-hexanediol from a carboxylic acid mixture obtained as by-product in the oxidation of cyclohexane to cyclohexanone/cyclohexanol with oxygen or oxygen-comprising gases and by aqueous extraction of the reaction mixture and comprising adipic acid, 6-hydroxycaproic acid and small amounts of 1,4-cyclohexanediols by esterification of the acids and hydrogenation, by a) reacting the mono- and dicarboxylic acids in the aqueous dicarboxylic acid mixture with a low molecular weight alcohol to form the corresponding carboxylic esters, b) conducting a first distillation to remove excess alcohol and low boilers from the esterification mixture obtained, c) conducting a second distillation to separate the bottom product into an ester fraction which is essentially free from 1,4-cyclohexanediols and a fraction which includes at least the larger proportion of the 1,4-cyclohexanediols, d) subjecting the ester fraction essentially free from 1,4-cyclohexanediols to a catalytic hydrogenation, and e) subjecting the hydrogenation effluent to a distillation to recover 1,6-hexanediol in a conventional manner, comprises using an aqueous dicarboxylic acid mixture comprising more than 20 ppm of cobalt and more than 40 ppm of phosphorus in the form of phosphate and passing this aqueous dicarboxylic acid mixture through a cation exchanger and after the esterification of step (a) through an anion exchanger.

6 Claims, 2 Drawing Sheets

METHOD FOR PRODUCING HEXANEDIOL-1,6

This application is the national phase of PCT/EP99/03193, filed May 10, 1999.

DESCRIPTION

The present invention relates to a process for preparing 1,6-hexanediol from a carboxylic acid mixture obtained in the oxidation of cyclohexane to cyclohexanone/cyclohexanol with oxygen and by aqueous extraction of the reaction mixture and comprising adipic acid and 6-hydroxycaproic acid by esterification of the acids and hydrogenation, by using a carboxylic acid mixture comprising cobalt and phosphate as impurities and passing this mixture through a cation exchanger to remove these impurities and then passing the esterification mixture through an anion exchanger.

WO 97/31882 discloses a process for preparing 1,6-hexanediol from aqueous solutions of carboxylic acids obtained in the oxidation of cyclohexane to cyclohexanone/cyclohexanol with oxygen and aqueous extraction by a) reacting the mono- and dicarboxylic acids in the aqueous dicarboxylic acid mixture with a low molecular weight alcohol to form the corresponding carboxylic esters, b) conducting a first distillation to remove excess alcohol and low boilers from the esterification mixture obtained, c) conducting a second distillation to separate the bottom product into an ester fraction which is essentially free from 1,4-cyclohexanediols and a fraction which includes at least the larger proportion of the 1,4-cyclohexanediols, d) subjecting the ester fraction essentially free from 1,4-cyclohexanediols to a catalytic hydrogenation, and e) subjecting the hydrogenation effluent to a distillation to recover 1,6-hexanediol in a conventional manner.

It has now been found that aqueous carboxylic acid mixtures comprising cobalt in the form of $Co^{2+}$ and/or $Co^{3+}$ ions in amounts of, for example, 20 to 300 ppm and phosphate in amounts of, for example, 40 to 1500 ppm as impurities from the oxidation are not directly suitable for the process of WO 97/31882.

It is an object of the present invention to provide a process for removing the aforementioned impurities from the feed solution in a simple and economical manner.

We have found that this object is achieved according to the invention by a process for preparing 1,6-hexanediol from a carboxylic acid mixture obtained as by-product in the oxidation of cyclohexane to cyclohexanone/cyclohexanol with oxygen or oxygen-comprising gases and by aqueous extraction of the reaction mixture and comprising adipic acid, 6-hydroxycaproic acid and small amounts of 1,4-cyclohexanediols by esterification of the acids and hydrogenation, by a) reacting the mono- and dicarboxylic acids in the aqueous dicarboxylic acid mixture with a low molecular weight alcohol to form the corresponding carboxylic esters, b) conducting a first distillation to remove excess alcohol and low boilers from the esterification mixture obtained, c) conducting a second distillation to separate the bottom product into an ester fraction which is essentially free from 1,4-cyclohexanediols and a fraction which includes at least the larger proportion of the 1,4-cyclohexanediols, d) subjecting the ester fraction essentially free from 1,4-cyclohexanediols to a catalytic hydrogenation, and e) subjecting the hydrogenation effluent to a distillation to recover 1,6-hexanediol in a conventional manner, the invention comprising using an aqueous dicarboxylic acid mixture comprising more than 20 ppm of cobalt and more than 40 ppm of phosphorus in the form of phosphate and passing this aqueous dicarboxylic acid mixture through a cation exchanger and after the esterification of step (a) through an anion exchanger.

Although the use of ion exchangers to remove cations or anions is common prior art, the process of the invention is surprising because of the absence of undesirable reactions during the dewatering between the cation exchanger and the anion exchanger. The acidic cation exchanger converts phosphate into phosphoric acid, so that the distillative dewatering of the carboxylic acid solution treated with the cation exchanger was likely to give rise to acid-catalyzed reactions of 6-hydroxycaproic acid, such as elimination of the hydroxyl group or polyester formation. However, neither is the case. In fact, the phosphoric acid formed even has the advantage of acting as esterification catalyst, making it possible to reduce the amount of sulfuric acid which is added as esterification catalyst.

Aside from the treatment of the aqueous carboxylic acid mixture with the cation exchanger and the treatment of the esterification reaction mixture with the anion exchanger, the process of the invention is described in all details in WO 97/31882, incorporated herein by reference. Any statement made therein shall also apply here without any restriction whatsoever.

BRIEF DESCRIPTION OF DRAWINGS

The process described therein will be described once more herein with its variants A (FIG. 1) and variant B (FIG. 2) in order that the location of the treatment with the cation exchanger or anion exchanger may be better indicated. (The terms overhead and as bottom product indicate respectively withdrawal above and below the feed).

VARIANT A

Figure 1:
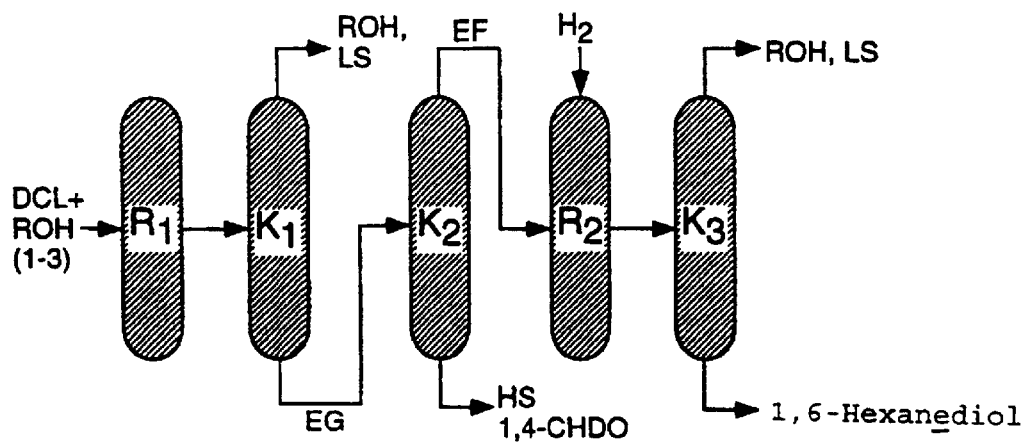

As illustrated in FIG. 1, the dicarboxylic acid solution (DCL), optionally after dewatering, is fed together with a $C_1$–$C_3$ alcohol, preferably methanol, into the esterification reactor $R_1$, where the carboxylic acids are esterified. The esterification mixture obtained then passes into column $K_1$, where the excess alcohol (ROH), water and low boilers (LS) are distilled off overhead and the ester mixture (EG) is withdrawn as bottom product and fed into the fractionating column $K_2$. This column fractionates the mixture into an ester fraction (EF), which is essentially free from 1,4-cyclohexanediols, and a bottom fraction, consisting of high boilers (HS) and 1,4-cyclohexanediols (1,4-CHDO). The ester fraction (EF) is then catalytically hydrogenated in the hydrogenating reactor $R_2$ and the hydrogenation mixture is separated in the distillation column $K_3$ into alcohol (ROH), low boilers (LS) and pure 1,6-hexanediol.

VARIANT B

Figure 2:
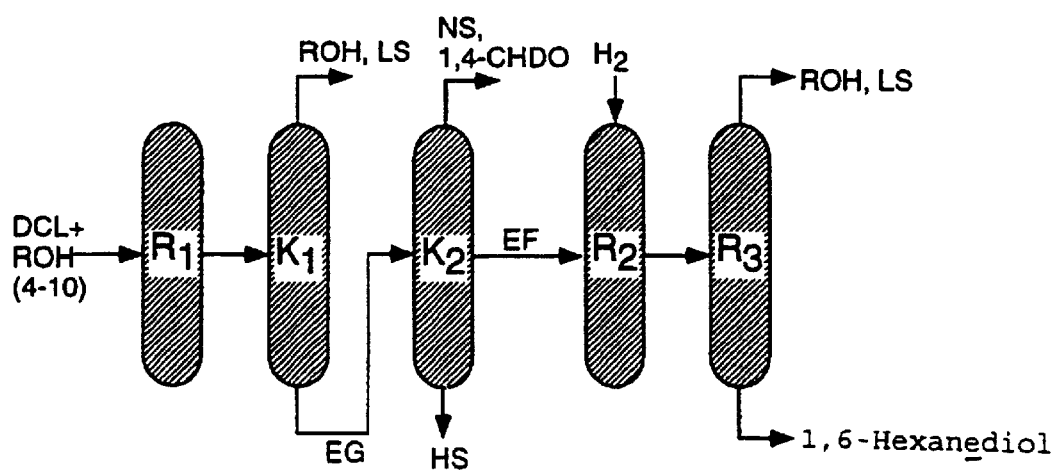

On esterifying with alcohols having 4 or more carbon atoms, especially n- or i-butanol, the process of FIG. 2 differs only in that the fractionating column K$_2$ will separate the ester mixture (EG) into a head product of low boilers (NS), including the 1,4-cyclohexanediols (1,4-CHDO), and an ester fraction (EF) which is essentially free from 1,4-cyclohexanediol and which is obtained as a sidestream fraction or as a bottom product comprising the ester fraction and fed into the hydrogenating stage (R$_2$).

Figure 3:
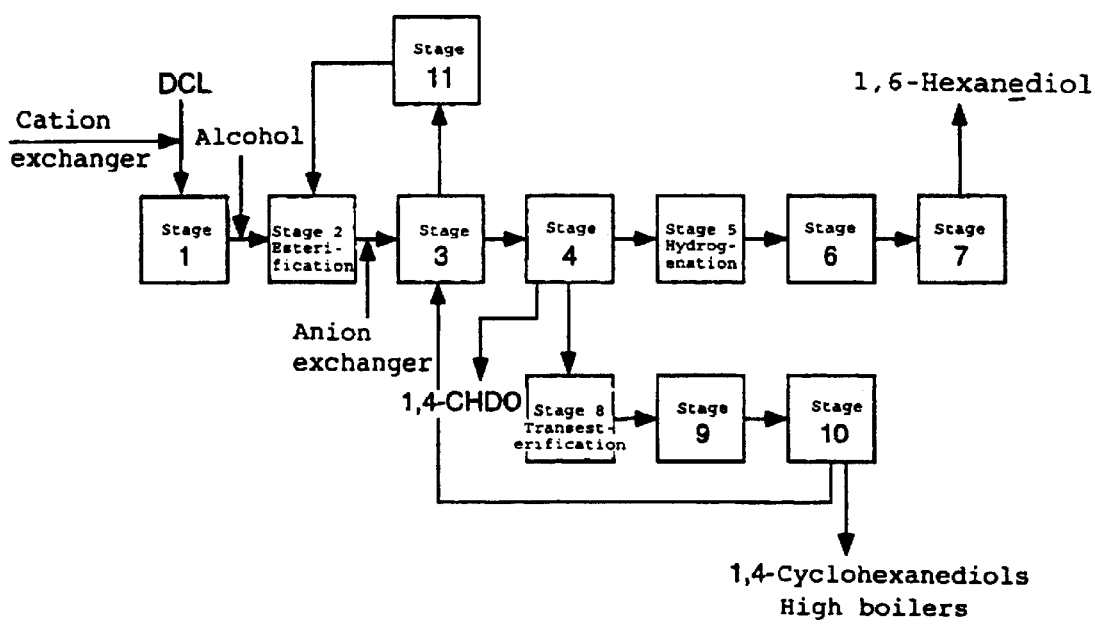
FIG. 3 is a flow diagram of the claimed process.

The process will now be more particularly described. FIG. 3 breaks down the individual process steps into further stages, of which stages 0, 2, 2a, 3, 4, 5, 6, 7 are essential for the process and stages 3 and 4 and also 6 and 7 can be combined. Stages 8, 9, 10 and 11 are optional, but may be sensible to improve the economics of the process.

The below-detailed treatment with the cation exchanger takes place as stage 0 ahead of stage 1.

The dicarboxylic acid solution (DCL) is generally an aqueous solution having a water content of from 20 to 80%. Since an esterification reaction is an equilibrium reaction, it is usually sensible, especially in the case of an esterification with methanol, for example, to remove existing water before the reaction, especially when water cannot be removed, for example azeotropically, during the esterification reaction. The dewatering in stage 1 can be effected for example with a membrane system or preferably by means of a distillation apparatus, in which water is removed overhead and higher monocarboxylic acids, dicarboxylic acids and 1,4-cyclohexanediols are removed as bottom product at from 10 to 250° C., preferably at from 20 to 200° C., particularly preferably at from 30 to 200° C., and a pressure of from 1 to 1500 mbar, preferably from 5 to 1100 mbar, particularly preferably from 20 to 1000 mbar. The base of column temperature for the distillation is preferably such that the bottom product can be withdrawn as a liquid. The water content in the bottom product of the column can be within the range from 0.01 to 10% by weight, preferably from 0.01 to 5% by weight, particularly preferably from 0.01 to 1% by weight.

The water can be separated off in such a way that the water is obtained predominantly acid-free, or the lower monocarboxylic acids present in the DCL—formic acid, essentially—can very largely be distilled off with the water in order that they may not bind esterification alcohol in the esterification.

The carboxylic acid stream from stage 1 has mixed into it an alcohol having from 1 to 10 carbon atoms, in variant A alcohols having from 1 to 3 carbon atoms, i.e., methanol, ethanol, propanol or isopropanol, preferably methanol, and in variant B alcohols having 4 to 10, especially from 4 to 8, carbon atoms, particularly preferably n-butanol, isobutanol, n-pentanol and i-pentanol.

The mixing ratio of alcohol to carboxylic acid stream (mass ratio) can be within the range from 0.1 to 30, preferably within the range from 0.2 to 20, particularly preferably within the range from 0.5 to 10.

This mixture passes as a melt or solution into the reactor of stage 2, where the carboxylic acids are esterified with the alcohol. The esterification reaction can be carried out at from 50 to 400° C., preferably at from 70 to 300° C., particularly preferably at from 90 to 200° C. An external pressure can be applied, but preferably the esterification is carried out under the autogenous pressure of the reaction system. The esterification apparatus used can be a stirred tank or a flow tube or it is possible to use a plurality of each. The residence time required for the esterification reaction is within the range from 0.3 to 10 hours, preferably within the range from 0.5 to 5 hours. The esterification reaction can be carried out without a catalyst, but the addition of a catalyst is preferred to raise the reaction rate. The catalyst which is added can be a homogeneously dissolved catalyst or a solid catalyst. Examples of homogeneous catalysts are sulfuric acid, phosphoric acid, hydrochloric acid, sulfonic acids, such as p-toluenesulfonic acid, heteropolyacids such as tungstophosphoric acid or Lewis acids such as aluminum, vanadium, titanium, boron compounds. Preference is given to mineral acids, especially sulfuric acid. The weight ratio of homogeneous catalyst to carboxylic acid melt is generally within the range from 0.0001 to 0.5, preferably within the range from 0.001 to 0.3.

Suitable solid catalysts include acidic or superacidic materials, for example acidic and superacidic metal oxides such as $SiO_2$, $Al_2O_3$, $SnO_2$, $ZrO_2$ or sheet-silicates or zeolites, which may all be doped with mineral acid radicals such as sulfate or phosphate to increase their acid strength, or organic ion exchangers having sulfonic acid or carboxylic acid groups. Solid catalysts can be used in the form of a fixed bed or as suspension.

The water formed in the course of the reaction is advantageously removed continuously, for example by means of a membrane or by distillation.

The completeness of the conversion of the free carboxyl groups present in the carboxylic acid melt is ascertained by measuring the acid number (mg of KOH/g) after the reaction. The acid number, not counting any acid added as catalyst, is within the range from 0.01 to 50, preferably within the range from 0.1 to 10. Not all the carboxyl groups present in the system are present as esters of the alcohol used; some can be present in the form of dimeric or oligomeric esters, for example with the OH end of hydroxycaproic acid.

The below-detailed treatment with the anion exchanger takes place as stage 2a between stage 2 and stage 3.

The esterification mixture is fed into stage 3, a membrane system or preferably a distillation column. When a dissolved acid is used as catalyst for the esterification reaction, the esterification mixture will advantageously be neutralized with a base, from 1 to 1.5 base equivalents being added per acid equivalent of catalyst. The bases used are generally alkali or alkaline earth metal oxides, carbonates, hydroxides or alkoxides or amines, with a solvent or dissolved in the esterification alcohol.

When stage 3 is a column, the column is preferably fed between the head stream and the bottom product stream. The head product, which is taken off at pressures from 1 to 1500 mbar, preferably from 20 to 1000 mbar, particularly preferably from 40 to 800 mbar, and temperatures within the range from 0 to 150° C., preferably from 15 to 90° C., especially from 25 to 75° C., includes the excess esterification alcohol ROH, water and, for example, corresponding esters of formic acid, acetic acid and propionic acid. This stream can either be incinerated or preferably be worked up further in stage 11.

The bottom product obtained is an ester mixture consisting predominantly of esters of the alcohol ROH with dicarboxylic acids, such as adipic acid and glutaric acid, hydroxycarboxylic acids, such as 6-hydroxycaproic acid and 5-hydroxyvaleric acid, and also oligomers and free or esterified 1,4-cyclohexanediols. It can be sensible to allow a residual level of water and/or alcohol ROH of up to 10% by weight in each case in the ester mixture. The bottom product temperatures range from 70 to 250° C., preferably from 80 to 220° C., particularly preferably from 100 to 190° C.

The stage 3 exit stream which has been substantially freed from water and esterification alcohol ROH is fed into stage 4, a distillation column where the feed is generally located between the low boiling components and the high boiling components. The column is operated at temperatures from 10 to 300° C., preferably from 20 to 270° C., particularly preferably from 30 to 250° C., and pressures from 1 to 1000 mbar, preferably from 5 to 500 mbar, particularly preferably from 10 to 200 mbar.

In variant A, i.e., esterification with $C_1$–$C_3$ alcohols, especially methanol, then, the stream from stage 3 is separated into a head fraction to be hydrogenated and a bottom fraction which includes the 1,4-cyclohexanediols.

The head fraction consists predominantly of residual water and residual alcohol ROH, esters of the alcohol ROH with monocarboxylic acids, predominantly $C_3$–$C_6$ monocarboxylic acids, esters with hydroxycarboxylic acids, such as 6-hydroxycaproic acid, 5-hydroxyvaleric acid, and especially the diesters with dicarboxylic acids, such as adipic acid, glutaric acid and succinic acid, plus 1,2-cyclohexanediols, caprolactone and valerolactone.

The components mentioned can be separated off overhead and be fed into the hydrogenation (stage 5) or, in a further preferred embodiment, be separated in the column into a head stream of predominantly residual water and residual alcohol and also the abovementioned esters of the $C_3$–$C_5$ carboxylic acids, and a sidestream of predominantly the abovementioned esters of $C_6$ carboxylic acids and dicarboxylic acids, which then pass into the hydrogenation.

The high boiling components of the stream from stage 4, consisting predominantly of 1,4-cyclohexanediols or their esters, dimeric or oligomeric esters and also the undefined, partly polymeric, ingredients of DCL, are separated off via the stripping portion of the column. They can be obtained together or in such a way that the 1,4-cyclohexanediols are predominantly removed via a sidestream in the stripping portion and the remainder via the bottom product. The 1,4-cyclohexanediols thus obtained can be used for example as starting materials for active compounds. The high boiling components, with or without the 1,4-cyclodiol content, can either be incinerated or, in a preferred embodiment, pass into stage 8 for transesterification.

In variant B, i.e., the esterification with $C_4$–$C_{10}$ alcohols, especially n- or i-butanol, the stream from stage 3 can be separated in stage 4 into a head fraction comprising the 1,4-cyclohexanediols, a sidestream comprising predominantly the $C_6$ esters, which passes into the hydrogenation, and a bottom product stream which comprises high boilers and which may pass into the optional stage 8.

The head fraction consists predominantly of residual alcohol ROH, $C_{1–C3}$ monoesters of the alcohol ROH, valerolactone and 1,2- and 1,4-cyclohexanediols.

The sidestream comprises predominantly diesters of succinic acid, glutaric acid and adipic acid and also monoesters of 5-hydroxyvaleric acid and 6-hydroxycaproic acid. This sidestream can be taken off either above or else below the column feed point and be introduced into the hydrogenation (stage 5).

The bottom product stream with oligomeric esters and miscellaneous high boilers may, as in variant A, either be incinerated or advantageously pass into stage 8.

In a further embodiment, stage 4 comprises separating the $C_6$ esters off together with either the bottom product stream and then, in a further column, either separating them as bottom product from the above-described head fraction, which consists predominantly of residual alcohol ROH, $C_1$–$C_3$ monoesters of the alcohol ROH, valerolactone and 1,2- and 1,4-cyclohexanediols, or as head stream from the high boilers.

The stage 4 exit fraction which is free or substantially free of 1,4-cyclohexanediols, either the overall stream or the sidestream which comprises mainly esters of $C_6$ acids, is passed into the hydrogenating stage 5.

Stages 3 and 4 can be combined, especially if only minor amounts are processed. This can be accomplished, for example, by obtaining the $C_6$ ester stream in a batchwise fractional distillation, again without 1,4-cyclohexanediols passing into the hydrogenation feed stream.

The hydrogenation is carried out catalytically either in the gas or in the liquid phase. Suitable catalysts include in principle all homogeneous and heterogeneous catalysts suitable for hydrogenating carbonyl groups, such as metals, metal oxides, metal compounds or mixtures therof. Examples of homogeneous catalysts are described for example in Houben-Weyl, Methoden der Organischen Chemie, Volume IV/1c, Georg Thieme Verlag Stuttgart, 1980, p. 45–67), and examples of heterogeneous catalysts are described for example in Houben-Weyl, Methoden der Organischen Chemie, Volume IV/1c, p. 16 to 26.

Preference is given to using catalysts comprising one or more elements of transition groups I and VI to VIII of the periodic table of the elements, preferably copper, chromium, molybdenum, manganese, rhenium, ruthenium, cobalt, nickel and palladium, particularly preferably copper, cobalt or rhenium.

The catalysts may consist solely of the active components or the active components may be applied to supports. Suitable support materials include for example $Cr_2O_3$, $Al_2O_3$, $SiO_2$, $ZrO_2$, $ZnO_2$, BaO and MgO or mixtures thereof.

Particular preference is given to catalysts as described in EP 0 552 463. These are catalysts which in the oxidic form have the composition $Cu_aAl_bZr_cMn_dO_x$ where a>0, b>0, c≧0, d>0, a>b/2, b>a/4, a>c and a>d and x is the number of oxygen ions required to preserve electrical neutrality per unit formula. These catalysts can be prepared for example according to the directions of EP 552 463 by precipitating sparingly soluble compounds from solutions comprising the corresponding metal ions in the form of their salts. Suitable salts include for example halides, sulfates and nitrates. Suitable precipitants include all agents which lead to the formation of such insoluble intermediates as are convertible by thermal treatment into the oxides. Particularly suitable intermediates are the hydroxides and carbonates or bicarbonates, so that particularly preferred precipitants include alkali metal carbonates or ammonium carbonate. An important element of the preparation of the catalysts is the thermal treatment of the intermediates at temperatures within the range from 500° C. to 1000° C. The BET surface area of the catalysts is within the range from 10 to 150 m²/g.

Preference is given to using heterogeneous catalysts, which are employed either as fixed bed or in the form of a suspension. When the hydrogenation is carried out in the gas phase and over fixed bed catalyst, the general conditions employed are temperatures from 150 to 300° C. at pressures from 1 to 100 bar, preferably from 15 to 70 bar. It is advantageous in this connection to use sufficient hydrogen as hydrogenant and carrier gas for starting materials, intermediates and products never to become liquid during the reaction. The excess hydrogen is preferably recirculated, although a small part may be bled out of the system as an off-gas to remove inerts, for example methane. It is possible to use one reactor or a plurality of consecutive reactors.

A hydrogenation in the liquid phase using a fixed bed or suspended catalyst is generally carried out at temperatures from 100 to 350° C., preferably from 120 to 300° C., and pressures from 30 to 350 bar, preferably from 40 to 300 bar.

The hydrogenation can be carried out in one reactor or in a plurality of consecutive reactors. The hydrogenation in the liquid phase over a fixed bed can be carried out not only in the trickle mode but also in the upflow mode. A preferred embodiment utilizes a plurality of reactors, the predominant portion of the esters being hydrogenated in the first reactor, which is preferably operated with liquid recycle to remove heat, while the subsequent reactor or reactors is or are preferably operated without recirculation to complete the conversion.

The hydrogenation may be carried out batchwise but is preferably carried out continuously.

The hydrogenation effluent consists essentially of 1,6-hexanediol and the alcohol ROH. Further ingredients, especially if the entire low boiling exit stream of stage 4 under variant A has been used, are 1,5-pentanediol, 1,4-butanediol, 1,2-cyclohexanediols and also small amounts of monoalcohols having from 1 to 6 carbon atoms and water.

This hydrogenation effluent is separated in stage 6, which is for example a membrane system or preferably a distillation column, into the alcohol ROH, which additionally comprises the substantial proportion of the other low boiling components, and a stream which predominantly comprises 1,6-hexanediol as well as 1,5-pentanediol and the 1,2-cyclohexanediols. Stage 6 is operated at a pressure from 10 to 1500 mbar, preferably from 30 to 1200 mbar, particularly preferably from 50 to 1000 mbar, head temperatures from 0 to 120° C., preferably from 20 to 100° C., particularly preferably from 30 to 90° C., and base of column temperatures from 100 to 270° C., preferably from 140 to 260° C., particularly preferably from 160 to 250° C. The low boiling stream can either be returned directly into the esterification of stage 2 or pass into stage 8 or into stage 11.

The 1,6-hexanediol stream is purified in a column in stage 7. 1,5-Pentanediol, any 1,2-cyclohexanediols and any other low boilers present are removed overhead. If the 1,2-cyclohexanediols and/or 1,5-pentanediol are to be recovered as additional products of value, these can be separated in a further column. Any high boilers present are removed from the system via the bottom product. 1,6-Hexanediol is removed from a side stream of the column with a purity of at least 99%. Stage 7 is operated at pressures from 1 to 1000 mbar, preferably from 5 to 800 mbar, particularly preferably from 20 to 500 mbar, head temperatures from 50 to 200° C., preferably from 60 to 150° C., and base of column temperatures from 130 to 270° C., preferably from 150 to 250° C.

If only comparatively small amounts of 1,6-hexanediol are produced, then stages 6 and 7 can also be combined in a batchwise fractional distillation.

To optimize the economics of hexanediol production, it is sensible to recover the esterification alcohol ROH and reuse it for esterification. To this end, the exit stream of stage 3 and/or 6, which comprises predominantly the alcohol ROH, for example methanol, can be worked up in stage 11. This is advantageously accomplished using a column in which components which have a lower boiling point than the alcohol ROH are removed overhead and water and components with a higher boiling point than the alcohol ROH are removed via the bottom product, while the alcohol ROH itself is recovered in a sidestream. The column is advantageously operated at from 500 to 5000 mbar, preferably at from 800 to 3000 mbar.

In a further preferred embodiment of the process, the high boiling stream from stage 4 (variant A) is used for raising the total yield of 1,6-hexanediol, based on adipic acid and 6-hydroxycaproic acid in the DCL used. To this end, the dimeric and oligomeric esters of adipic acid and hydroxycaproic acid are reacted with further amounts of the alcohol ROH in the presence of a catalyst in stage 8. The weight ratio of alcohol ROH to the bottom product stream from stage 4 is within the range from 0.1 to 20, preferably within the range from 0.5 to 10, particularly preferably within the range from 1 to 5. Suitable catalysts include in principle those already described for the esterification in stage 2. However, preference is given to using Lewis acids. Examples are compounds or complexes of aluminum, of tin, of antimony, of zirconium or of titanium, such as zirconium acetylacetonate or tetraalkyl titanates, e.g., tetraisopropyl titanate, which are employed in concentrations from 1 to 10000 ppm, preferably from 50 to 6000 ppm, particularly preferably from 100 to 4000 ppm, based on the transesterification mixture. Titanium compounds are particularly preferred.

The transesterification can be carried out batchwise or continuously, in one or more reactors, in consecutive stirred tanks or tubular reactors at from 100 to 300° C., preferably at from 120 to 270° C., particularly preferably from 140 to 240° C., and the corresponding autogenous pressures. The residence times required range from 0.5 to 10 hours, preferably from 1 to 4 hours.

This stream from stage 8 can for example be reintroduced into stage 3 in the case of esterification with methanol. To avoid buildups, especially of 1,4-cyclohexanediols, it is then necessary for a bleed stream of the high boilers to be removed batchwise or continuously from stage 4. Another possibility is not to recycle the stream from stage 8 to stage 3, but, similarly to stage 3, to separate it in a stage 9 into predominantly alcohol ROH, which can then pass back into stage 2, 8 or 11, and a stream comprising the esters.

This ester stream can in principle (subject to the proviso of the avoidance of buildups of 1,4-cyclohexanediols) be returned into stage 4 or is preferably separated in a further stage 10 into the esters of the $C_6$ acids and (in terms of amount rather insignificantly) the esters of the $C_5$ acids on the one hand, which can either be introduced into stage 4 or directly into stage 5, and high boilers on the other, which include the 1,4-cyclohexanediols, and then the high boilers are removed from the system.

This makes it possible to obtain more than 95% yields of more than 99% pure 1,6-hexanediol.

In detail, the starting material is treated with the cation exchanger by preferably using a fixed bed ion exchanger which can be a strongly acidic, gellike cation exchanger or preferably a strongly acidic, macroporous, macroreticular resin.

The treatment with the cation exchanger is preferably carried out in two alternately operated fixed beds, which can also be connected in series and of which initially only the first bed is loaded with cobalt. When the concentration of cobalt in the effluent has reached 10 ppm, at the latest, the aqueous carboxylic acid solution is additionally passed through the second bed until the first bed is exhausted, i.e., the effluent from the first bed has for example reached more than 90% of the feed concentration or there has been a complete breakthrough by cobalt which is no longer absorbed. The feed stream is then routed directly onto the second fixed bed. The originally first bed is then regenerated, preferably after product previously still retained in the ion exchanger has been washed out with water and the eluate has been returned into the starting material stream, and, after regeneration, assumes the function of the downstream bed.

The cation exchangers to be used according to the invention make it possible to reduce cobalt contents to values of 1 ppm or less.

The cation exchangers used are conventional exchanger resins, for example weakly acidic, strongly acidic or chelate-formers, as described for example in "Ionenaustauscher, Dr. U. Dorfner, 1970, Walter de Gruyter & Co, Berlin". Particular preference is given to strongly acidic cation exchangers.

Suitable cation exchangers are in particular cation exchangers which contain sulfonic acid groups or carboxylic acid groups supported on a polymer comprising polystyrene crosslinked with divinylbenzene. Depending on the divinylbenzene content the ion exchanger resins are gellike (divinylbenzene content ~4%) or macroporous (divinylbenzene content ~12–20%).

It is also possible to use cation exchangers based on acrylic acid or methacrylic acid crosslinked with divinylbenzene or resins produced by condensation of formaldehyde and phenol.

Specific examples are Lewatit® CNP 80, Lewatit SP 112, Lewatit K 2621, Lewatit 10 P 80 from Bayer and Amberlite® 252C, Amberlite 1200 and Duolite® AR C9652 or Amberlyst® WET from Rohm & Haas, as described in these companies' product literature.

To remove the unwanted anions, i.e., especially phosphate and also sulfate (from sulfuric acid as esterification catalyst), it is preferable to 2 alternately operated fixed beds, which can also be connected in series, as described for the cation exchanger. The esterification mixture is passed through the first bed until the phosphate content in the effluent reaches 10 ppm, for example. This can be ascertained by an increase in the conductivity and a decrease in the pH. Upon attainment of this limit a second anion exchanger bed is added in the downstream position until the first ion exchanger is exhausted, i.e., until the phosphate concentration in the effluent has reached, for example, 50% of the feed value or a complete breakthrough takes place. This is generally the case when the pH has dropped below 4. At this point, the first bed is switched off and regenerated. Prior to regeneration, the ester mixture retained in the ion exchanger is advantageously washed out. This is generally accomplished by flushing with nitrogen, methanol and again nitrogen and returning the eluate into the esterification stage. The regenerated first bed then assumes the function of the downstream bed.

The anion exchangers used can again be conventional, strongly basic, weakly basic, medium basic gellike or macroporous ion exchangers as described in "Ionenaustauscher, Dr. U. Dorfner, 1970, Walter de Gruyter & Co, Berlin". These are generally weakly basic macroporous ion exchangers, preferably of particularly low basicity. These are for example anion exchangers comprising polystyrene resins crosslinked with divinylbenzene and having tertiary amino groups as functional groups. For the purposes of this invention it is also possible to use ion exchangers having strongly basic groups (quaternary amines) or having medium basic groups. Similarly, anion exchangers based on acrylic acid or methacrylic acid crosslinked with divinylbenzene or resins produced by condensation of formaldehyde and phenol are suitable.

Specific examples are Amberlite IRA® 92, IRA 96, Lewatit® MP 64, MP 500, Amberset 4200 or Lewatit® MP 62 from Bayer AG and Rohm & Haas (cf. these companies' product leaflets).

The inventive treatment of the starting material or of the esterification mixture makes it possible to operate the process of WO 97/31882 in a trouble-free and continuous manner even with a starting solution comprising cobalt and phosphate. Elimination of the sulfate ions produces additional advantages, since the formation of, for example, $K_2SO_4$ can be avoided in the neutralization. The presence of $K_2SO_4$ in the waste stream to be incinerated necessitates a special, very cost-intensive design for the incinerating furnace. Potassium sulfate forms eutectic mixtures with the customary furnace linings, so that the reduced melting point of the lining greatly reduces the service life of the boiler.

The invention will now be more particularly described by reference to the following Example. The Example is set forth by way of illustration and is not intended to limit the scope of the invention.

EXAMPLE (Variant A)

Stage 0 (cation exchange)

4.7 kg/h of dicarboxylic acid solution were pumped at a superficial velocity of 14 m/h through a column, 20 mm in diameter, packed with a 2000 mm bed of Amberlyst® 15 WET and maintained at 60° C., and sampled on the exit side to determine the cobalt and iron concentrations. The feed solution had a cobalt content of 115 ppm (and an iron content of 9 ppm). Both cations were reduced to a level of <1 ppm. The total operating capacity achieved until breakthrough was 0.823 mol/l, which corresponds to 1.703 eq/l.

A superficial velocity of about 33 m/h gave a total operating capacity of 0.70 mol/l, corresponding to 1.45 eq/l. Again, the exit concentrations of cobalt and iron were both less than 1 ppm.

Stage 1 (dewatering):

0.1 kg/h of dicarboxylic acid solution (consisting essentially of adipic acid, 6-hydroxycaproic acid, 1,4-cyclohexanediols, glutaric acid, 5-hydroxyvaleric acid, formic acid, water and having a residual cobalt content of <1 ppm) were distilled continuously in a distillation apparatus (three-plate bubble cap column with external oil heating circuit, oil temperature 150° C., plate volume about 25 ml each, feed above the bubble cap trays) fitted with a packed column (about 4 theoretical plates, no reflux at the head). The head product was obtained at 0.045 kg/h with a formic acid content of the water of about 3%. The bottom product stream (5.5 kg) had a water content of about 0.4%.

Stage 2 (esterification):

5.5 kg/h of the bottom product stream of stage 1 were continuously reacted with 8.3 kg/h of methanol and 14 g/h of sulfuric acid in a tubular reactor 0.7 m in length and 1.8 cm in internal diameter (residence time 2.7 h). The acid number of the effluent minus sulfuric acid was about 10 mg of KOH/g.

Stage 2a (anion exchange)

550 g/h of esterification effluent were pumped at a superficial velocity of about 2 m/h through a column packed with Lewatit® MP 62 (Bayer) and maintained at 35° C. The exit solution was sampled to determine the level of sulfur and phosphorus. Both the anions were found to be depleted to <1 ppm from feed solution concentrations of 1050 ppm of sulfate and 950 ppm of phosphate. The total capacity reached was 1.2 mol/l, corresponding to 1.84 eq/l (on the basis of $SO_4^{2-}$ and $H_2PO_4^-$). A sustained run was carried out over 21 cycles without any observable decrease in the operating capacity. Depletion to below 1 ppm was achieved even at a superficial velocity of 7 m/h.

Stage 3 (removal of excess alcohol and of water):

The esterification stream from stage 2, comprising <1 ppm of phosphate and <1 ppm of sulfate, was distilled in a 20 cm packed column (1015 mbar, 65° C. head of column temperature, up to 125° C. base of column temperature). 7.0 kg were withdrawn overhead. The amount of bottom product obtained was 6.8 kg.

Stage 4 (fractionation; 1,4-cyclohexanediol removal):

The bottom product stream from stage 3 was subjected to a fractional distillation in a 50 cm packed column (1 mbar, 70–90° C. head of column temperature, up to 180° C. base of column temperature). The bottom product (1.9 kg) contained virtually all 1,4-cyclohexanediols.

The amount of low boilers distilled off was 0.6 kg (1,2-cyclohexanediols, valerolactone, methyl 5-hydroxyvalerate, dimethyl glutarate, dimethyl succinate, etc.). A fraction containing predominantly dimethyl adipate and methyl 6-hydroxycaproate was obtained in an amount of 4.3 kg.

The head stream representing the ester fraction is introduced into hydrogenating stage 5.

Stage 5 (hydrogenation):

4.3 kg of the $C_6$ ester fraction from stage 4 were continuously hydrogenated in a 25 ml reactor over a catalyst (70% by weight of CuO, 25% by weight of ZnO, 5% by weight of $Al_2O_3$), which had previously been activated in a stream of hydrogen at 180° C. The feed was 20 g/h, the pressure 220 bar and the temperature 220° C. The ester conversion was 99.5%, and the 1,6-hexanediol selectivity was more than 99%.

Alternatively, the ester fraction was continuously hydrogenated in a two-stage reactor battery (1st reactor 2.5 l of catalyst, trickle mode 250 bar, product recycle:feed=10:1, 220–230° C.; 2nd reactor 0.5 l of catalyst, trickle mode straight path, 260 bar, 220° C.). The catalyst used was composed of CuO (60%), $Al_2O_3$ (30%) and $Mn_2O_3$ (10%) and had previously been activated at 180° C. The feed rate was 1 kg/h. The hexanediol selectivity was more than 99% at a conversion of 99.5%.

Stages 6 and 7:

4.0 kg of the hydrogenation effluent of stage 5 were subjected to a fractional distillation (distillation flask fitted with 70 cm packed column, reflux ratio 2). 1 kg of methanol was distilled off at 1013 mbar. Reducing the pressure to 20 mbar caused predominantly the 1,2-cyclohexanediols and 1,5-pentanediol to distil over. Thereafter (boiling point 146° C.), 1,6-hexanediol passed over at a purity of 99.8% (residual content predominantly 1,5-pentanediol).

The yield was the same as from the use of a DCL starting material which, by virtue of the process used to obtain it, already contained less than 20 ppm of cobalt and less than 40 ppm of phosphate and therefore was not treated with the cation and anion exchanger.

We claim:

1. A process for preparing 1,6-hexanediol from a carboxylic acid mixture obtained as by-product in the oxidation of cyclohexane to cyclohexanone/cyclohexanol with oxygen or oxygen-comprising gases and by aqueous extraction of the reaction mixture and comprising adipic acid, 6-hydroxycaproic acid and small amounts of 1,4-cyclohexanediols by esterification of the acids and hydrogenation, by a) reacting the mono- and dicarboxylic acids in the aqueous dicarboxylic acid mixture with a low molecular weight alcohol to form the corresponding carboxylic esters, b) conducting a first distillation to remove excess alcohol and low boilers from the esterification mixture obtained, c) conducting a second distillation to separate the bottom product into an ester fraction which is essentially free from 1,4-cyclohexanediols and a fraction which includes at least the larger proportion of the 1,4-cyclohexanediols, d) subjecting the ester fraction essentially free from 1,4-cyclohexanediols to a catalytic hydrogenation, and e) subjecting the hydrogenation effluent to a distillation to recover 1,6-hexanediol in a conventional manner, which comprises using an aqueous dicarboxylic acid mixture comprising more than 20 ppm of cobalt and more than 40 ppm of phosphorus in the form of phosphate and passing this aqueous dicarboxylic acid mixture through a cation exchanger and after the esterification of step (a) through an anion exchanger.

2. A process as claimed in claim 1, wherein the pretreatment is carried out with fixed bed ion exchangers.

3. A process as claimed in claim 1, wherein the pretreatment is carried out with two alternately operated fixed beds, which can also be connected in series, until the cobalt content of the outflow from the first bed is more than 90% of the inflow concentration, at which point the first bed is switched off and regenerated to assume the function of the downstream bed.

4. A process as claimed in claim 1, wherein the pretreatment is carried out with 2 consecutive anion exchanger beds until the phosphate content of the outflow from the first bed is more than 50% of the inflow concentration, at which point the first bed is switched off and regenerated to assume the function of the downstream bed.

5. A process as claimed in claim 1, wherein the cation exchanger prior to regeneration is washed product-free with water and the wash liquor is mixed into the starting dicarboxylic acid solution.

6. A process as claimed in claim 1, wherein the anion exchanger prior to regeneration is washed with methanol and the wash liquor is returned into the esterification.

* * * * *